United States Patent
Bevinakatti

(10) Patent No.: US 11,135,148 B2
(45) Date of Patent: *Oct. 5, 2021

(54) HAIR FIXATIVES INCLUDING STARCH ESTER BASED POLYGLUCOSE POLYMERS

(71) Applicant: Akzo Nobel Chemicals International B.V., Arnhem (NL)

(72) Inventor: Hanamanthsa Bevinakatti, Somerset, NJ (US)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/100,675

(22) PCT Filed: Dec. 17, 2014

(86) PCT No.: PCT/EP2014/078227
§ 371 (c)(1),
(2) Date: Jun. 1, 2016

(87) PCT Pub. No.: WO2015/091650
PCT Pub. Date: Jun. 25, 2015

(65) Prior Publication Data
US 2016/0296454 A1    Oct. 13, 2016

Related U.S. Application Data

(60) Provisional application No. 61/919,066, filed on Dec. 20, 2013.

(30) Foreign Application Priority Data

Feb. 14, 2014   (EP) .................................. 14155145

(51) Int. Cl.
| | |
|---|---|
| *A61K 8/73* | (2006.01) |
| *A61Q 5/06* | (2006.01) |
| *A61K 8/85* | (2006.01) |
| *A61K 8/34* | (2006.01) |

(52) U.S. Cl.
CPC .............. *A61K 8/732* (2013.01); *A61K 8/34* (2013.01); *A61K 8/85* (2013.01); *A61Q 5/06* (2013.01)

(58) Field of Classification Search
CPC . A61K 8/732; A61K 8/34; A61K 8/85; A61Q 5/06
See application file for complete search history.

(56) References Cited

U.S. PATENT DOCUMENTS

| | | | | |
|---|---|---|---|---|
| 3,790,664 A * | 2/1974 | Krochock | ............. | A61K 8/732 132/203 |
| 4,011,392 A * | 3/1977 | Rudolph | ................. | C08B 31/04 106/207.1 |
| 4,061,611 A * | 12/1977 | Glowaky | ............. | C09D 103/06 524/51 |
| 4,225,476 A | 9/1980 | Hammer et al. | | |
| 5,789,570 A * | 8/1998 | Buchholz | ................ | A61L 15/28 536/107 |
| 6,001,473 A * | 12/1999 | Atkinson | ............. | C09D 103/06 427/208.4 |
| 6,344,183 B2 * | 2/2002 | Paul | ....................... | A61K 8/046 424/45 |
| 6,413,505 B1 | 7/2002 | Vitale et al. | | |
| 6,800,675 B1 * | 10/2004 | Pfalz | ......................... | C08F 2/24 524/47 |
| 7,517,924 B1 * | 4/2009 | Rimsa | ....................... | C08L 3/06 523/128 |
| 2001/0007655 A1 | 7/2001 | Paul et al. | | |
| 2008/0146792 A1 * | 6/2008 | Wang | ...................... | C08B 31/04 536/107 |
| 2010/0029928 A1 * | 2/2010 | De Vries | ................ | A61K 8/046 536/109 |
| 2011/0064678 A1 * | 3/2011 | Knappe | ................ | A61K 8/8152 424/47 |
| 2012/0258052 A1 * | 10/2012 | Mueller | ................. | A61K 8/046 424/47 |

FOREIGN PATENT DOCUMENTS

| | | |
|---|---|---|
| CN | 1234225 A | 11/1999 |
| CN | 102206288 A | 10/2011 |
| EP | 0 948 958 A2 | 10/1999 |
| EP | 1 949 885 A1 | 7/2008 |
| FR | 2778559 A1 | 11/1999 |
| GB | 810306 | 3/1959 |

(Continued)

OTHER PUBLICATIONS

Sweedman et al. Structure and physicochemical properties of octenyl succinic anhydride modified starches: A review. Carbohydrate Polymers (2013) 92:905-920 (online Sep. 29, 2012). (Year: 2013).*
Ackar et al. Starch Modification by Organic Acids and Their Derivatives: Review . Molecules 2015, 20:19554-19570. (Year: 2015).*
Tomasik et al. Chemical Modification of Starch. Advances in Carbohydrate Chemistry and Biochemistry (2004) vol. 59:175-403. (Year: 2004).*
European Search Report for EP 14155145.7, dated May 23, 2014.
International Search Report and Written Opinion for PCT/EP2014/078227, dated May 20, 2015.

(Continued)

*Primary Examiner* — Robert A Wax
*Assistant Examiner* — Olga V. Tcherkasskaya
(74) *Attorney, Agent, or Firm* — Norris McLaughlin, P.A.

(57) ABSTRACT

A hair fixative composition includes at least one carboxylated starch ester based polyglucose polymer, an alcohol based solvent system, and a cosmetically acceptable additive, wherein the polyglucose polymer is soluble in the alcohol based solvent system. The polyglucose polymer is obtained by reacting at least one starch ester with at least one anhydride.

13 Claims, No Drawings

(56) References Cited

FOREIGN PATENT DOCUMENTS

JP      H11-322552 A    11/1999
JP      H11-335247 A    12/1999

OTHER PUBLICATIONS

O.N.A. Investigación, Database Mintel GNPD [Online], Nourishing Conditioner, Nov. 1, 2010, Database Record ID. 1431176, Product Information: Ingredients, 3 pgs., XP-002723845.

Communication pursuant to Article 94(3) EPC issued in counterpart EP Application No. 14 821 139.4 dated Oct. 2, 2018.

Product Specification Sheet, GLUCIDEX® 1, obtained on the website roquette.com, pp. 1-2, revised Jan. 22, 2019.

Product Specification Sheet, GLUCIDEX® 2, obtained on the website roquette.com, pp. 1-2, revised Jul. 5, 2018.

Specification Sheet, STAR-DRI® 1, obtained on the website tateandlyle.com, pp. 1-6, revised Apr. 20, 2018.

\* cited by examiner

HAIR FIXATIVES INCLUDING STARCH ESTER BASED POLYGLUCOSE POLYMERS

This application is a national stage filing under 35 U.S.C. § 371 of PCT/EP2014/078227, filed Dec. 17, 2014, which claims priority to U.S. Provisional Patent Application No. 61/919,066 filed Dec. 20, 2013, and European Patent Application No. 14155145.7, filed Feb. 14, 2014, the contents of which are each incorporated herein by reference in their entireties.

FIELD OF THE INVENTION

The invention relates to personal care compositions comprising carboxylated starch ester polyglucose polymers. More specifically, the invention relates to hair fixative compositions comprising carboxylated starch ester polyglucose polymers that are soluble in alcohol based solvent systems.

BACKGROUND OF THE INVENTION

Polymers used in personal care applications, such as hair styling and hair fixing, have conventionally been made using synthetic materials. In order for the polymers to be suitable in such personal care applications, they must be soluble in alcohol based systems, and in the case of aerosol based hair sprays, they must also be compatible with the propellant. Conventional synthetic polymers are generally inexpensive and provide acceptable performance; however, because they are not made from renewable resources, they are not sustainable. In addition, replicating the cost and performance of synthetic polymers is not easy.

Accordingly, there is a need for personal care polymers made from renewable sources that provide equal to or better performance at comparable costs than their synthetic alternatives and that are soluble in alcohol based systems, such as ethanol based systems and optionally, that are compatible with propellants, such as dimethyl ether.

SUMMARY OF THE INVENTION

In an aspect, the present invention relates to a hair fixative composition comprising at least one carboxylated starch ester based polyglucose polymer; an alcohol based solvent system; and a cosmetically acceptable additive. The polyglucose polymer is obtained by reacting at least one starch ester with an anhydride, such as a cyclic anhydride or an acylic anhydride or mixtures thereof, and the polyglucose polymer is soluble in the alcohol based solvent system. The starch ester may be obtained by reacting starch with at least one acyclic anhydride, at least one cyclic anhydride or mixtures thereof.

In another aspect, the present invention relates to a method of preparing a hair fixative composition comprising reacting at least one starch ester with an anhydride, such as a cyclic anhydride or an acylic anhydride or mixtures thereof, to form a starch ester based polyglucose polymer. In a further step, the method comprises dissolving or suspending the starch ester based polyglucose polymer in the alcohol based solvent system. The starch ester may be obtained by reacting starch with at least one acyclic anhydride, at least one cyclic anhydride or mixtures thereof.

In yet another aspect, the present invention relates to the use of the carboxylated starch ester based polyglucose polymer as defined herein as a hair fixative polymer in a hair fixative composition, as well as a method of styling hair, comprising applying the carboxylated starch ester based polyglucose polymer as defined herein to hair.

DETAILED DESCRIPTION OF THE INVENTION

As used herein, the recitations of numerical ranges by endpoints include all numbers subsumed within that range (e.g., 1 to 5 includes 1, 1.5, 2, 2.75, 3, 3.80, 4, 5, etc.). In addition, it is to be understood that for embodiments including ranges as described herein, the respective lower endpoints and respective upper endpoints described include combinations of the various lower and upper endpoints. For example, for ranges of 1 to 20 and 5 to 10, respectively, the ranges also include, without limitation, 1 to 10 and 5 to 20.

The hair fixative compositions of the present invention comprise carboxylated starch ester based polymers that combine the features of having a polysaccharide backbone having attached at least one ester group and at least one carboxyl functional group.

It has been found that the carboxylated starch ester based polyglucose polymers can provide hair fixative polymers that are not only made from renewable sources but that can also provide equal to or better hair styling performance, such as spray rate, viscosity, stiffness and high humidity curl retention, especially as hair spray polymers, at comparable costs than their synthetic alternatives. The inventive polymers are soluble in an alcohol based system and, optionally, they are also compatible with hair styling propellants.

The present invention generally relates to hair fixative compositions including at least one carboxylated starch ester based polyglucose polymer having the following structure (I):

$$\left[ \begin{array}{c} O-R \\ \phantom{x} \\ OH \phantom{xxx} O \phantom{x} H \\ \phantom{x} \\ OR \phantom{x} OR \end{array} \right]_n \quad I$$

wherein R=H, $R_H$ or $R_A$ or combinations thereof, wherein at least one R is $R_A$ and wherein $R_H$ is: —CO—$R^1$ wherein $R^1$ is $C_1$-$C_{21}$ alkyl group, preferably a $C_1$ to $C_{10}$ alkyl group, and more preferably $C_1$-$C_3$; and $R_A$ is: (a) —CO—$CH_2$—CH($R^2$)—COOH wherein $R^2$=H or $C_1$-$C_{18}$ alkyl or alkenyl group, preferably a $C_6$-$C_{18}$ alkenyl group, and more preferably a $C_8$, $C_{12}$ or $C_{18}$ alkenyl group; or b) —CO—CH=CH—COOH; or c) —CO—CH—C(=$CH_2$)—COOH; or d) —CO—$C_6H_4$—COOH or e) —CO—$C_6H_8$—COOH; and wherein n=10-500, more preferably 30-400, and still more preferably 30-150. The hair fixative compositions further include an alcohol based solvent system and a cosmetically acceptable additive wherein the polyglucose polymer is soluble in the alcohol based solvent system.

In the above formula (I), $R_H$ represents hydrophobic groups and $R_A$ represents groups having acid functionality and, optionally, hydrophobic functionality. In general, the carboxylated starch ester based polyglucose polymers are formed by reacting an ester of the polysaccharide, such as starch acetate, starch propionate, starch butyrate, starch acetate butyrate and starch acetate propionate with an anhydride, such as a cyclic anhydride or an acyclic anhydride. In an embodiment, the anhydride may be a substituted anhydride or an unsubstituted anhydride. In a further embodiment, the anhydride is more preferably a substituted anhydride. Suitable anhydrides include, but are not limited to such as a succinic anhydride, an alkenyl succinic anhydride, maleic anhydride, itaconic anhydride, phthalic anhydride or tetrahydrophthalic anhydride to give a succinate derivative, a maleate derivative, or an itaconate derivative, phthalate derivative or tetrahydropthalate derivative or combinations thereof.

In an embodiment of the present invention, the polysaccharide ester may be modified with a substituted anhydride in an amount from about 15 wt % to about 50 wt % based on weight percent of the polysaccharide ester. In another embodiment, the polysaccharide ester preferably may be modified with the substituted anhydride in an amount from about 20 wt % to about 45 wt %, and in yet another embodiment, more preferably from about 25 wt % to about 35 wt %.

Non-limiting examples of carboxylated starch ester based polyglucose polymers according to the invention include polymers of formula I wherein $R_H$ is: —CO—$R^1$ wherein $R^1$ is a $C_1$-$C_{21}$ alkyl group, preferably a $C_1$ to $C_{10}$ alkyl group, and more preferably a $C_1$-$C_3$ alkyl group and $R_A$ is: (a) —CO—$CH_2$—CH($R^2$)—COOH wherein $R^2$=H or $C_1$-$C_{18}$ alkyl or alkenyl group, preferably a $C_6$-$C_{18}$ alkenyl group, and more preferably a $C_8$, $C_{12}$ or $C_{18}$ alkenyl group, and wherein n=10-500, more preferably 30-400, and still more preferably 30-150; wherein $R_H$ is: —CO—$R^1$ wherein $R^1$ is a $C_1$-$C_{22}$ alkyl group, preferably a $C_1$ to $C_{10}$ alkyl group, and more preferably a $C_1$-$C_3$ alkyl group and $R_A$ is: b) —CO—CH=CH—COOH, wherein n=10-500, more preferably 30-400, and still more preferably 30-150; $R_H$ is —CO—$R^1$ wherein $R^1$ is a $C_1$-$C_{22}$ alkyl group, preferably a $C_1$ to $C_{10}$ alkyl group, and more a preferably $C_1$-$C_3$ alkyl group and $R_A$ is: c) —CO—CH—C(=$CH_2$)—COOH, and wherein n=10-500, more preferably 30-400, and still more preferably 30-150; wherein $R_H$ is —CO—$R^1$ wherein $R^1$ is a $C_1$-$C_{22}$ alkyl group, preferably a $C_1$ to $C_{10}$ alkyl group, and more preferably a $C_1$-$C_3$ alkyl group and $R_A$ is: d) —CO—$C_6H_4$—COOH, and wherein n=10-500, more preferably 30-400, and still more preferably 30-150; where in $R_H$ is —CO—$R^1$ wherein $R^1$ is a $C_1$-$C_{21}$ alkyl group, preferably a $C_1$ to $C_{10}$ alkyl group, and more preferably a $C_1$-$C_3$ alkyl group and $R_A$ is: (e) —CO—$C_6H_8$—COOH, and wherein n=10-500, more preferably 30-400, and still more preferably 30-150. In an embodiment, combinations of the above are also included. In an embodiment, the polyglucose polymers suitable for use in the present invention include, but are not limited to, starch acetate succinate octenyl succinate, starch acetate phthalate octenyl succinate or combinations thereof.

In an embodiment, the carboxylated starch ester based polyglucose polymers of the present invention may be present in the hair fixative composition in an amount from about 1 weight percent to about 10 weight percent, based on the weight of the hair fixative composition. In another embodiment, the polyglucose polymers are present in an amount from about 2 weight percent to about 8 weight percent. In yet another embodiment, the polyglucose polymers are present in an amount from about 3 weight percent to about 6 weight percent.

In a further aspect, the present invention provides a polyglucose polymer obtained by reacting a starch with an anhydride, which may be acyclic or cyclic, and then further reacting the reaction mixture with another anhydride, which may also be acyclic or cyclic to obtain the polyglucose polymer. For example, in an embodiment the starch may be reacted with at least one acyclic anhydride to form a starch ester, which may be isolated or further reacted in situ, and then the reaction mixture or the isolated starch ester is further reacted with a cyclic anhydride to form the polyglucose polymer.

In one embodiment of the invention, the starch material that is first reacted with an anhydride, which anhydride may be acyclic or cyclic, is not a starch ether ester material.

In an embodiment, preferably the starch ester is obtained by reacting a starch with at least one acyclic anhydride, such as such as acetic, propionic or butyric anhydride or mixtures thereof, forming starch acetate, starch propionate or starch butyrate and/or mixtures thereof. In a further embodiment, the polyglucose polymer is obtained by reacting a starch ester with a cyclic anhydride, such as succinic anhydride, an alkenyl succinic anhydride, maleic anhydride, itaconic anhydride, phthalic anhydride or tetrahydrophthalic anhydride and/or mixtures thereof.

The polyglucose polymers of the present invention are based on starch or starch derivatives. The starch polymers can be prepared from any starch source, including, but not limited to corn, banana, barley, amaranth, arrowroot, canna, sorghum, wheat, rice, tapioca, potato, sago, pea or sweet potato. In an embodiment, the starch is from a corn, potato, wheat, rice or tapioca source. In another embodiment, the starch is from potato or corn source. Suitable starches and starch derivatives include, but are not limited to, saccharides or derivatives thereof. Suitable saccharides include, for example, oligosaccharides and polysaccharides (e.g., maltodextrins, corn syrups, pyrodextrins and starches) and their hydrogenated versions, such as hydrogenated starch or hydrogenated hydrolyzed starch. In an embodiment of the invention, the polyglucose polymers are obtained from maltodextrin, pyrodextrin or a low molecular weight starch or oxidized starch. It has been found that polyglucose polymers based on starch do not work well when the polyglucose polymer is not soluble in the alcohol based solvent system. Accordingly, in embodiments of the invention, the weight average molecular weight of the starch is preferably less than about 500,000 daltons. Starches having such exemplary molecular weights are water soluble. In another embodiment, the weight average molecular weight (Mw) of the starch may be less than about 200,000 daltons. In yet another preferred embodiment, the weight average molecular weight of the starch may be less than about 100,000 daltons. In yet another preferred embodiment, the weight average molecular weight of the starch may be less than about 50,000 daltons. In an embodiment, the weight average molecular weight of the starch is about 1,000 daltons or greater, in another embodiment preferably about 5,000 daltons or greater and in yet another embodiment more preferably about 10,000 daltons or greater.

In an even further embodiment, the polyglucose polymers may be obtained from maltodextrins, pyrodextrins and chemically modified versions of maltodextrins and pyrodextrins. In an embodiment, the polysaccharide is preferably maltodextrin having a dextrose equivalent (DE) of less than about 25, in another embodiment preferably about 20 or less and in yet another embodiment more preferably about 15 or less. In an embodiment, when the polysaccharide is maltodextrin, it may have a DE of about 1 or more, even more preferably about 5 or more and in yet another embodiment about 10 or more. The term dextrose equivalent, as used herein, is a measure of the amount of reducing sugars present in a sugar product, relative to glucose, and is a well known term of art.

In an embodiment, the starches used as the starting materials may also have a high amylose content. As used herein, the term "high amylose" is intended to include starch containing at least about 50%, in another embodiment preferably at least 70%, and in yet another embodiment more preferably at least 80% by weight amylose. The amylose portions of fractionated starches are also suitable.

In an embodiment, the starch ester based polyglucose polymer has a total degree of substitution (D.S.) in a range from about 1.0 to about 3.0. In another embodiment, the polyglucose polymer has a total D.S. in a range from about 1.5 to about 3.0, and in yet another embodiment from about 2.0 to about 2.9. The number of substituted hydroxyl groups per anhydroglucose unit is expressed as the degree of substitution (D.S.).

The carboxylated starch ester based polyglucose polymers can be used as obtained from their natural source or they can be chemically modified. Chemical modification includes hydrolysis by the action of acids, enzymes, oxidizers or heat, hydrogenation, esterification or etherification.

In another aspect, the hair fixative compositions comprise at least one polyglucose polymer and an alcohol based solvent system. As used herein, an alcohol based solvent system comprises at least one alcohol and may include further optional components, such as water, propellant or other non-alcohol, non aqueous solvents. The polyglucose polymer must be soluble in the alcohol based solvent system. In an embodiment, the amount of alcohol present in the solvent system may be about 1 weight percent or greater, in another embodiment preferably about 15 weight percent or greater, and in yet another embodiment, more preferably from about 25 weight percent or greater. In an embodiment, the amount of alcohol present in the solvent system may be about 99 weight percent or less, in another embodiment preferably about 50 weight percent or less and in yet another embodiment more preferably about 40 weight percent or less, based on total weight of the solvent system. In another embodiment, the alcohol solvent system may be anhydrous.

In an embodiment of the invention, the hair fixative composition will include no more than about 85% of volatile organic compounds (VOC), such as alcohol and/or propellant with the remainder of the solvent being water. In another embodiment, the hair fixative compositions will comprise no more than about 55% volatile organic compounds.

For purposes of the present invention, the term "soluble" means that from about 1 to about 10 weight percent and in another embodiment preferably from about 3 to about 6 weight percent, of the polyglucose polymer is soluble, with or without neutralization, in the alcohol based solvent system. In an embodiment, alcohol based solvent systems suitable for use in the present invention comprise at least one $C_1$-$C_6$ straight or branched chain alcohol or mixtures thereof and, optionally, water, optionally one or more propellants and optionally one or more other non-alcohol, non-aqueous solvents. In an embodiment, the alcohol solvent in the alcohol based solvent system comprises at least one $C_2$ or $C_3$ alcohol or mixtures thereof. In an embodiment the solvent system is substantially free of non-alcohol organic solvents. In one embodiment the solvent system is substantially free of acetone. As used herein with respect to the solvent system, the term "substantially free" means that the solvent system contains less than 50%, alternatively less than 40%, alternatively less than 30%, alternatively less than 20%, alternatively less than 10%, alternatively less than 5%, of the non-alcohol organic solvent or acetone, respectively.

In an embodiment of the invention, the hair fixative compositions further include at least one neutralizing agent. In an embodiment of the invention, the polyglucose polymer is generally at least about 50% neutralized. In another embodiment, the polyglucose polymer is at least about 70% neutralized, and in an even further embodiment, the fixative polymer is 100% neutralized. Suitable basic neutralizing agents compatible with the composition can be employed, even inorganic materials such as sodium or potassium hydroxide. Generally organic amines or alkanolamines are readily used for neutralization. In an embodiment, the neutralizing agents include, but are not limited to ammonia; primary, secondary and tertiary amines; alkanolamines; and, hydroxyamines such as 2-amino-2-methyl-propanol and 2-amino-2-methyl-1,3-propanediol, mono-, di- and tri-long chain fatty amines containing a $C_4$ to $C_{24}$ hydrocarbon chain, ethoxylates and propoxylates long chain ($C_4$ to $C_{24}$) fatty amines and mixtures thereof. In another embodiment, the neutralizing agents include aminomethylpropanol, and dimethyl stearamine, inorganic materials, such as sodium hydroxide and potassium hydroxide, and triethanolamine. In an embodiment of the invention, the neutralizing agent is an organic amine or alkanolamine. In an embodiment, combinations of neutralizing agents may also be used.

In an embodiment, the hair fixative compositions have spray rate in a range from about 0.3 to about 1.5 grams/sec. in an 80% VOC system at 3.5% solids and 40% dimethyl ether (DME), in another embodiment, preferably from about 0.5 grams/sec. to about 1.2 grams/sec., and in another embodiment, more preferably from 0.75 about to 0.9 grams/sec.

In addition to the above-described solvent systems, the present invention may further optionally include one or more propellants. In an embodiment of the invention where the hair fixative composition is a spray application, the polyglucose polymer is compatible with the propellant. By compatible, it is meant that the polyglucose polymer in the solvent system does not phase separate when the solution is mixed with the propellant. In an embodiment, the polyglucose polymer is preferably compatible with dimethyl ether as the propellant. For purposes of the present invention, the term "compatible" means that up to about 10 weight percent of the polyglucose polymer is soluble in the hair fixative composition that includes the propellant. In another embodiment, the polyglucose polymer is preferably soluble from about 1 to about 10 weight percent, and in yet another embodiment, from about 2 to about 8 weight percent and in still yet another embodiment from about 3 to about 6 weight percent in the hair fixative composition that includes the propellant.

Spray applications of the present invention require a mechanical device or pressurized aerosol container to generate the spray. The devices can be manual such as a pump or squeeze bottle or typical aerosol device such as bag-on-nozzle or pressurized can. If a pressurized can is used then the hair styling formulations of the present invention may further include a propellant. Such propellants include, without limitation, ethers, such as dimethyl ether; one or more lower boiling hydrocarbons such as $C_3$-$C_6$ straight and branched chain hydrocarbons, for example, propane, butane, and isobutane; halogenated hydrocarbons, such as, hydrofluorocarbons, for example, trichlorofluoromethane, dichlorodifluoromethane, 1,1-difluoroethane and 1,1,1,2-tetrafluoroethane, present as a liquefied gas; and the compressed gases, for example, nitrogen, air and carbon dioxide as well as mixtures of these propellants. In an embodiment of the invention, the propellant is present in an amount of about 25% to about 80% by weight of the hair fixative composition including the solvent system. In a further embodiment, the propellant is present in an amount of about 30% to about 60% by weight. Alternatively, in certain spray applications, such as bag-on-nozzle spray applications or pump spray applications, such optional propellants are not required. The hair fixative compositions of the present invention include, but are not limited, to aerosol and non-aerosol hairsprays.

In general, in another aspect of the invention, the method for preparing the hair spray formulations of this invention includes dissolving, suspending or diluting the polyglucose polymer in the selected solvents, adding any modifying agents depending on the desired properties, and thereupon combining the resulting solution with the selected aerosol propellant.

With regard to amounts of the various components, in an embodiment the final hair fixative compositions may contain the starch ester based polyglucose polymer in a concentration ranging from about 1 to 10%, by weight; the alcohol based solvent in a concentration ranging from about 30 to 90%, by weight; and, if included, the optional propellant concentration in a range from 20 to 75%, by weight. In another embodiment the final hair fixative compositions may contain the polyglucose polymer in a concentration ranging from about 2 to 8%, by weight; the solvent in a concentration ranging from about 25 to 55%, by weight; and, if included, the optional propellant concentration in a range from 25 to 55%, by weight.

In yet another aspect, the present invention relates to the use of the carboxylated starch ester based polyglucose polymer as defined herein as a hair fixative polymer in a hair fixative composition, as well as a method of styling hair, comprising applying the carboxylated starch ester based polyglucose polymer as defined herein to hair. In one embodiment the hair fixative composition is in the form of a spray, in one embodiment the spray is an aerosol spray, in one embodiment the spray is a non-aerosol spray. In one embodiment the hair fixative composition is in the form of a mousse. In one embodiment the hair fixative composition is in the form of a gel.

The application of the hair fixative compositions of the present invention may be prior to, during, or after the desired hair style has been achieved.

As used herein, the acronym "OSA" means octenyl succinate anhydride; and the acronym "AMP" means aminomethylpropanol.

Optionally, cosmetically acceptable additives may be incorporated into the hair fixative compositions of this invention in order to modify certain properties thereof. One such optional additive may, in additional to the polyglucose polymer, a second polymer, such as a hair fixative polymer. Non-limiting examples of these additional hair fixative polymers include: from Akzo Nobel Surface Chemistry LLC, AMPHOMER® 4961, AMPHOMER®, and AMPHOMER® LV-71 polymers (octylacrylamide/acrylates/butylaminoethyl methacrylate copolymer), AMPHOMER® HC polymer (acrylates/octylacrylamide copolymer) and BALANCE® CR polymers (acrylates copolymer), BALANCE® 47 polymer (octylacrylamide/acrylates/butylaminoethyl methacrylate copolymer), RESYN® 28-2930 polymer (VA/crotonates/vinyl neodecanoate copolymer), RESYN® 28-1310 polymer (VA/Crotonates copolymer), FLEXAN® polymers (sodium polystyrene sulfonate), DynamX polymer (polyurethane-14 (and) AMP-Acrylates copolymer), RESYN® XP polymer (acrylates/octylacrylamide copolymer), STRUCTURE® 2001 (acrylates/steareth-20 itaconate copolymer) and STRUCTURE® 3001 (acrylates/ceteth-20 itaconate copolymer); from Ashland Inc., OMNIREZ-2000® (PVM/MA half ethyl ester copolymer), GANEX P-904® (butylated PVP), GANEX V-216® (PVP/hexadecene copolymer) GANEX® V-220 (PVP/eicosene copolymer), GANEX® WP-660 (tricontanyl PVP), GANTREZ® A425 (butyl ester of PVM/MA copolymer), GANTREZ® AN-119 PVM/MA copolymer, GANTREZ® ES 225 (ethyl ester of PVM/MA copolymer), GANTREZ® ES425 (butyl ester of PVM/MA copolymer), GAFFIX® VC-713 (vinyl caprolactam/PVP/dimethylaminoethyl methacrylate copolymer), GAFQUAT® 755 (polyquatemium-11), GAFQUAT® HS-100 (polyquaternium-28) AQUAFLEX® XL-30 (Polyimide-1), AQUAFLEX® SF-40 (PVP/Vinylcaprolactam/DMAPA Acrylates Copolymer), AQUAFLEX® FX-64 (Isobutylene/Ethylmaleimide/Hydroxyethylmaleimide Copolymer), ALLIANZ® LT-120 (Acrylates/C1-2 Succinates/Hydroxyacrylates Copolymer), STYLEZE® CC-10 (PVP/DMAPA Acrylates Copolymer), STYLEZE® 2000 (VP/Acrylates/Lauryl Methacrylate Copolymer), STYLEZE® W-20 (Polyquaternium-55), Copolymer Series (PVP/Dimethylaminoethylmethacrylate Copolymer), ADVANTAGE® S and ADVANTAGE® LCA (VinylcaprolactamNP/Dimethylaminoethyl Methacrylate Copolymer), ADVANTAGE® PLUS (VA/Butyl Maleate/Isobornyl Acrylate Copolymer); from BASF, The Chemical Company, ULTRAHOLD STRONG (acrylic acid/ethyl acrylate/t-butyl acrylamide), LUVIMER® 100P (t-butyl acrylate/ethyl acrylate/methacrylic acid), LUVIMER® 36D (ethyl acrylate/t-butyl acrylate/methacrylic acid), LUVIQUAT® HM-552 (polyquaternium-16), LUVIQUAT® HOLD (polyquaternium-16), LUVISKOL® K30 (PVP) LUVISKOL® K90 (PVP), LUVISKOL® VA 64 (PVP/VA copolymer) LUVISKOL® VA73W (PVP/VA copolymer), LUVISKOL® VA, LUVISET® PUR (Polyurethane-1), LUVISET® Clear (VP/MethacrylamideNinyl Imidazole Copolymer), LUVIFLEX® SOFT (Acrylates Copolymer), ULTRAHOLD® 8 (Acrylates/Acrylamide Copolymer), LUVISKOL® Plus (Polyvinylcaprolactam), LUVIFLEX® Silk (PEG/PPG-25/25 Dimethicone/Acrylates Copolymer); from The Dow Chemical Company, ACUDYNE® 180, ACUDYNE® 1000, and ACUDYNE® DHR (Acrylates/Hydroxyesters Acrylates Copolymer), ACUDYNE® SCP (Ethylenecarboxyamide/AMPSA/Methacrylates Copolymer), and the ACULYN® rheological modifiers; from Mitsubishi and distributed by Clariant Corporation, DIAFORMER® Z-301, DIAFORMER® Z-SM, and DIAFORMER® Z-400 (methacryloyl ethyl betaine/acrylates copolymer), from Nalco Company, FIXOMER® A-30 and FIXOMER® N-28 (INCI names: methacrylic acid/sodium acrylamidomethyl propane sulfonate copolymer); from The Lubrizol Corporation, FIXATE® G-100 (AMP-Acrylates/Allyl Methacrylate Copolymer), FIXATE PLUS® (Polyacrylates-14), FIXATE® SUPERHOLD (Polyacrylate-2 Crosspolymer), and FIXATE® FREESTYLE (Acrylates Crosspolymer-3) CARBOPOL® Ultrez 10 (Carbomer), CARBOPOL® Ultrez 20 (Acrylates/C10-30 Alkyl Acrylates Copolymer), AVALURE® AC series (Acrylates Copolymer), AVALURE® UR series (Polyurethane-2, Polyurethane-4, PPG-17/IPDI/DMPA Copolymer); polyethylene glycol; water-soluble acrylics; water-soluble polyesters; polyacrylamides; polyamines; polyquaternary amines; styrene maleic anhydride (SMA) resin; polyethylene amine; and other conventional polymer that is polar solvent soluble or that can be made soluble through neutralization with the appropriate base. A combination of one or more of the above hair fixative polymers is also contemplated as within the scope of the present invention. In an embodiment of the invention, the hair fixative polymer is preferably chosen from octylacrylamide/acrylates/butylaminoethyl methacrylate copolymers, acrylates/octylacrylamide copolymers, acrylates copolymer, octylacrylamide/acrylates/butylaminoethyl methacrylate copolymers, VA/crotonates/vinyl neodecanoate copolymers, VA/Crotonates copolymers, sodium polystyrene sulfonates, polyurethane-14 (and) AMP-Acrylates copolymers, acrylates/octylacrylamide copolymers, acrylates/steareth-20 itaconate copolymers, acrylates/ceteth-20 itaconate copolymers and combinations thereof.

In an embodiment of the invention, the optional hair fixative polymer may be present in the hair fixative composition in an amount of about 0.1 to 10% by weight based on total weight of the composition. In a further embodiment, the fixative polymer is present in an amount of about 1 to 10% by weight and in a further embodiment in an amount of about 1 to 7% by weight.

Further optional cosmetically acceptable additives may also include: plasticizers, such as glycols, phthalate esters and glycerine; silicones; emollients, lubricants and penetrants such as lanolin compounds, protein hydrolyzates and other protein derivatives, ethylene oxide adducts, and polyoxyethylene cholesterol; UV absorbers; dyes and other colorants; and, perfumes. Mixtures of these optional additives may also be included. As previously noted, the polymeric binders of this invention show little or no tendency to adversely chemically interact with such additives.

Further optional ingredients can include, but are not limited to, preservatives, colorants, fragrances, viscosity modifiers, vitamins, herbal extracts such as sterols, triterpenes, flavonoids, coumarins, non-glycosidic diterpenes (sterebins) spathulenol, decanoic acid, 8,11,14-ecosatrienoic acid, 2-methyloctadecane, pentacosane, octacosane, stigmasterol, bsitosterol, a- and b-amyrine, lupeol, b-amyrin acetate, and pentacyclic triterpene, include sunscreen actives such as such as a p-methoxycinnamate or an aminobenzoate (UVB absorber) or benzone or an anthranilate (UVA absorber medicaments, moisturizers, anti-itch or anti-dandruff ingredients and the like.

The resulting hair fixative formulations exhibit the characteristics required of such a product. They possess good antistatic properties, adhere well to hair, are easily removed by soapy water or shampoos, allow the hair to be readily recombed, do not yellow on aging, do not become tacky when exposed to high humidities, and have excellent curl retention under high humidity conditions.

The method for preparing the hair fixative compositions of the present invention can be performed in a number of different ways, and depends on the polyglucose polymer used. However, in a further aspect of the invention, the invention provides a nonlimiting method for preparing the hair fixative composition. The method comprises suspending or dissolving the polyglucose polymer in an alcohol based solvent systems, for example comprising one or more $C_1$-$C_6$ alcohols. In an embodiment, the method further includes neutralizing the solution with a neutralizing agent, such as aminomethylpropanol. In an embodiment, the one or more alcohols may comprise ethanol in combination with isopropanol or n-propanol, optionally in a weight ratio of about 80:20 to about 20:80 ethanol to isopropanol. In yet another embodiment, optionally, the method further includes the step of adding propellant to the composition. In a further optional step, the method may also include adding water to the composition either before, during or after suspending the polyglucose polymer in the alcohol or after the neutralizing step.

In an embodiment, the polyglucose polymers of the present invention are suitable for use in hair fixative compositions, such as hair sprays, mousses or gels.

The following examples are intended to exemplify the present invention but are not intended to limit the scope of the invention in any way. The breadth and scope of the invention are to be limited solely by the claims appended hereto.

Examples

General Synthesis Method for Polyglucose Polymers

Starch Acetate (or Propionate) Succinate Octenyl Succinate Polymers

A reaction vessel equipped with an agitator and condenser kept under nitrogen atmosphere and immersed in an oil bath for heating was charged with specified amount of (see Table 2) starch, acetic acid, sodium acetate (or sodium hydroxide) and acetic anhydride (or propionic anhydride). The amount of acetic (or propionic) anhydride was adjusted to take care of the moisture level generally present in the starch. The mixture was heated to 125-130° C. under stirring until the reaction showed completion as monitored by IR for the disappearance of the anhydride peak. Once all the acetic (or propionic) anhydride was reacted, the reaction mixture was cooled to about 100-110° C., OSA was added and the stirring continued at 110-115° C. until the reaction showed completion as monitored by IR for the disappearance of the anhydride peak due to OSA. Succinic anhydride was then added to the reaction mixture and the stirring was continued at 110-115° C. until all the succinic anhydride reacted as monitored by IR. The reaction mixture was then cooled to 70° C. and then poured to a vigorously stirred water (about 5 times the weight of the reaction mixture) at ambient temperature. After stirring for 30 min., the solid separated was filtered, washed with water until all the residual acetic acid was washed off and dried in oven at 45° C. overnight to give solid product.

Several other starch acetate (or propionate) succinate octenyl succinate using different starch source were prepared using essentially the same procedure mentioned above but using different quantities of raw-materials as detailed in Table 2 (Examples 1-13 and 16-26)

Starch Acetate Octenyl Succinate Phthalate Polymers

These were made using essentially the same procedure as described above, except that after all the acetic anhydride was reacted, specified amount of phthalic anhydride was added followed by OSA after 2 hours of addition of phthalic anhydride. Details of the raw-materials to make these products are detailed in Table 2, Examples 14, 15 and 27.

Table 1 summarizes the various Examples of polyglucose polymers synthesized in accordance with the present invention.

TABLE 1

Examples of Polyglucose Polymers[a]

| Example # | Starch used[b] | DS values (Theoretical)[c] | | | | | Acid value meq/g | Compatibility in | | Spray Rate g/sec |
|---|---|---|---|---|---|---|---|---|---|---|
| | | Acetic anhydride | Propionic anhydride | Succinic anhydride | OSA | Phthalic anhydride | | 80% VOC ethanol system[d] | 40% DME system[e] | |
| 1 | A | 1.62 | 0 | 0 | 0.52 | 0 | 1.76 | Insoluble | — | — |
| 2 | A | 1.6 | 0 | 1.58 | 0 | 0 | 3.79 | Soluble | Insoluble | — |
| 3 | A | 0 | 1.7 | 1.07 | 0 | 0 | 2.56 | Soluble | Insoluble | — |
| 4 | A | 2.19 | 0 | 1.05 | 0 | 0 | 2.70 | Soluble | Insoluble | — |
| 5 | A | 2.19 | 0 | 0.63 | 0 | 0 | 1.92 | Soluble | Insoluble | — |
| 6 | A | 2.19 | 0 | 0.42 | 0.21 | 0 | 2.20 | Soluble | Soluble | 0.80 |
| 7 | A | 2.19 | 0 | 0.21 | 0.42 | 0 | 2.28 | Soluble | Soluble | 0.83 |
| 8 | A | 2.19 | 0 | 0 | 0.63 | 0 | 2.04 | Soluble | Soluble | 0.76 |
| 9 | A | 2.19 | 0 | 0.32 | 0.32 | 0 | 1.98 | Soluble | Soluble | 0.89 |
| 10 | A | 2.19 | 0 | 0.32 | 0.52 | 0 | 2.52 | Soluble | Soluble | 0.86 |
| 11[f] | A | 2.19 | 0 | 0.21 | 0.42 | 0 | 2.02 | Soluble | Soluble | 0.84 |
| 12[f] | A | 2.19 | 0 | 0.21 | 0.52 | 0 | 2.34 | Soluble | Soluble | 0.79 |
| 13[f] | A | 2.19 | 0 | 0.32 | 0.32 | 0 | 1.94 | Soluble | Soluble | 0.78 |
| 14 | A | 2.1 | 0 | 0 | 0 | 0.6 | 1.55 | Soluble | Insoluble | — |
| 15 | A | 2.1 | 0 | 0 | 0.3 | 0.4 | 2.80 | Soluble | Soluble | 0.71 |
| 16 | A | 2.1 | 0 | 0 | 0.2 | 0.5 | 2.67 | Soluble | Soluble | 0.79 |
| 17 | B | 1.8 | 0 | 1.54 | 0 | 0 | 3.72 | Soluble | Insoluble | — |
| 18 | B | 0 | 1.8 | 1.54 | 0 | 0 | 2.66 | Insoluble | — | — |
| 19 | B | 0 | 1.84 | 1.05 | 0 | 0 | 2.36 | Soluble | Insoluble | — |
| 20 | B | 2.32 | 0 | 0.41 | 0.2 | 0 | 2.24 | Soluble | Soluble | 0.79 |
| 21 | B | 2.32 | 0 | 0.2 | 0.41 | 0 | 2.24 | Soluble | Soluble | 0.80 |
| 22[f] | C | 1.6 | 0 | 0 | 0.6 | 0 | 1.97 | Insoluble | — | — |
| 23[f] | C | 2.18 | 0 | 0.21 | 0.42 | 0 | 2.08 | Insoluble | — | — |
| 24[f] | C | 2.18 | 0 | 0.21 | 0.52 | 0 | 2.03 | Soluble | Soluble | 0.69 |
| 25[f] | C | 1.89 | 0 | 0.21 | 0.52 | 0 | 2.14 | Soluble | Soluble | 0.62 |
| 26[f] | C | 1.89 | 0 | 0.32 | 0.52 | 0 | 2.38 | Soluble | Soluble | 0.74 |
| 27 | C | 2.1 | 0 | 0 | 0 | 0.6 | 1.99 | Soluble | Insoluble | — |

[a]Unless otherwise mentioned, all reactions were carried out using sodium acetate as catalyst.
[b]A = Glucidex 1, a potato based maltodextrin from Roquette with DE 5 max;
B = Glucidex-2, a waxy maize based maltodextrin from Roquette with DE 5 max;
C = Star Dri-1, a waxy maize based maltodextrin from Tate & Lyle with DE 1.
[c]Amount of anhydride used to give the theoretically calculated Degree of Substation (DS) values on starch. The actual DS values obtained were not measured.
[d]Compatibility of 3.5 wt % polymer in 80:20 wt % ethanol:water with 90% neutralization level using AMP at ambient temp.
[e]Compatibility of 3.5 wt % polymer in 80% VOC ethanol system with 40% DME at ambient temp.
[f]Using NaOH instead of NaOAc as catalyst.

TABLE 2

Details of the raw-materials used to make the Polyglucose polymers[a]

| Example No. | Starch | Acetic Acid | Sodium Acetate[b] | Acetic anhydride | Propionic anhydride | Succinic Anhydride | OSA | Phthalic anhydride |
|---|---|---|---|---|---|---|---|---|
| 1 | 30 | 45 | 12.1 | 37.7 | 0 | 0 | 19.4 | 0 |
| 2 | 29.5 | 41 | 11.2 | 37.1 | 0 | 27.3 | 0 | 0 |
| 3 | 19.1 | 19 | 7.2 | 0 | 30.6 | 11.8 | 0 | 0 |
| 4 | 32.4 | 32 | 12.3 | 51 | 0 | 20 | 0 | 0 |
| 5 | 32.4 | 32 | 12.3 | 51 | 0 | 12 | 0 | 0 |
| 6 | 32.2 | 32 | 12.3 | 51 | 0 | 8 | 8.4 | 0 |
| 7 | 32.4 | 32 | 12.3 | 51 | 0 | 4 | 16.8 | 0 |
| 8 | 32.4 | 32 | 12.3 | 51 | 0 | 0 | 26.2 | 0 |
| 9 | 64.8 | 64 | 24.6 | 102 | 0 | 12 | 25.2 | 0 |
| 10 | 64.8 | 64 | 24.6 | 102 | 0 | 12 | 42 | 0 |
| 11 | 64.8 | 30 | 6[c] | 117.3 | 0 | 8 | 33.6 | 0 |
| 12 | 64.8 | 30 | 6[c] | 117.3 | 0 | 8 | 42 | 0 |
| 13 | 64.8 | 30 | 6[c] | 117.3 | 0 | 12 | 25.2 | 0 |
| 14 | 50.7 | 30 | 7.4 | 76.3 | 0 | 0 | 0 | 26.6 |
| 15 | 50.7 | 30 | 7.4 | 76.3 | 0 | 0 | 18.9 | 17.8 |
| 16 | 50.7 | 30 | 7.4 | 76.3 | 0 | 0 | 12.6 | 22.2 |
| 17 | 32.4 | 45 | 12.3 | 40.8 | 0 | 30 | 0 | 0 |
| 18 | 32.4 | 32 | 12.3 | 0 | 52 | 30 | 0 | 0 |
| 19 | 19.1 | 19 | 7.2 | 0 | 31.2 | 11.8 | 0 | 0 |
| 20 | 32.4 | 32 | 12.3 | 51 | 0 | 8 | 8.4 | 0 |
| 21 | 32.4 | 32 | 12.3 | 51 | 0 | 4 | 16.8 | 0 |
| 22 | 64.8 | 36 | 6[c] | 94.5 | 0 | 0 | 48.1 | 0 |
| 23 | 64.8 | 30 | 6[c] | 117.3 | 0 | 8 | 33.6 | 0 |

TABLE 2-continued

Details of the raw-materials used to make the Polyglucose polymers[a]

| Example No. | Starch | Acetic Acid | Sodium Acetate[b] | Acetic anhydride | Propionic anhydride | Succinic Anhydride | OSA | Phthalic anhydride |
|---|---|---|---|---|---|---|---|---|
| 24 | 64.8 | 30 | 6[c] | 117.3 | 0 | 8 | 42 | 0 |
| 25 | 64.8 | 20 | 6[c] | 106.1 | 0 | 8 | 42 | 0 |
| 26 | 64.8 | 20 | 6[c] | 106.1 | 0 | 12 | 42 | 0 |
| 27 | 51.6 | 80 | 7.4 | 81.5 | 0 | 0 | 0 | 26.6 |

[a]Weights shown are in grams.
[b]Unless otherwise mentioned, sodium acetate was used as a catalyst.
[c]Sodium hydroxide was used as a catalyst instead of sodium acetate.

A. Subjective Test Procedures

Subjective evaluations as provided in the Examples comparing AMPHOMER® polymer, each using 3.5 wt % of the polymers using 80 wt % VOC ethanol-water and 40 wt % DME or as otherwise identified using statistical design method at 95% confidence level were conducted. The results of the Subjective Evaluations conducted are reported in the Tables that follow as indicated.

The following procedures were used to conduct the evaluations of the subjective performance of the polyglucose polymers of the present invention.

Gloss:
Gently handle the swatches so as not to break the films. Visually inspect the swatches to determine which has more shine/gloss.

Stiffness:
Gently handle swatches and feel for differences in stiffness. Using two fingers, hold the middle of the swatch in a horizontal position—does one bend more than the other? Choose the one that is more rigid.

Spring:
While holding the swatch in one hand, gently pull on an edge with the other hand three times only. Look for spring back, and bounce. The more elastic the better the Spring.

Webbing:
While holding the swatch in both hands, gently pull outward on the edges approx. 4". (Do this three times only to avoid damage to the bonds. If the bonds are destroyed then the dry combing may appear to be easier to comb). The more net like the better the Webbing.

Dry Comb:
Comb through each swatch (5) times and evaluate ease of combing. Choose the one that combs more easily.

Flake:
Visually inspect both swatches after combing. Check the teeth of the comb for flake accumulation. Holding the swatch at the bound end run your fingernail down the length of the tress then inspect. Choose the one with more flakes.

Anti-Stat:
Holding swatch at bound end comb through vigorously 10 times then evaluate for extent of fly aways generated. Choose the one with more fly aways.

Feel:
Handle swatches and determine preference. Choose the one that feels more silky/cleaner.

TABLE 3

Subjective evaluation[a] of the Polyglucose Polymers of Examples 6-16, 20, 21 and 24-26 compared to AMPHOMER ® polymer using 3.5 wt % polymer using 80% VOC ethanol-water and 40% DME at 95% confidence level

| Example No. | Gloss | Stiffness | Spring | Webbing | Dry comb | Flake | Antistat | Feel |
|---|---|---|---|---|---|---|---|---|
| Glucidex-1 based polymers | | | | | | | | |
| 6 | − | = | = | = | = | = | + | − |
| 7 | = | = | − | − | = | = | = | = |
| 8 | − | − | = | = | = | − | = | = |
| 9 | − | = | = | = | + | + | + | = |
| 10 | = | = | = | = | = | = | = | = |
| 11 | − | = | − | − | = | = | = | = |
| 12 | − | − | − | = | + | + | = | + |
| 13 | − | = | = | = | = | = | + | + |
| 15[b] | − | − | − | − | = | = | = | = |
| 15[c] | = | − | − | = | + | = | + | = |
| 16[b] | = | − | − | = | + | − | = | = |
| 16[c] | − | = | − | = | = | − | + | = |
| Glucidex-2 based polymers | | | | | | | | |
| 20 | = | = | − | = | + | = | = | + |
| 21 | = | − | = | = | + | = | = | = |

TABLE 3-continued

Subjective evaluation[a] of the Polyglucose Polymers of Examples 6-16, 20, 21 and 24-26 compared to AMPHOMER ® polymer using 3.5 wt % polymer using 80% VOC ethanol-water and 40% DME at 95% confidence level

| Example No. | Gloss | Stiffness | Spring | Webbing | Dry comb | Flake | Antistat | Feel |
|---|---|---|---|---|---|---|---|---|
| Star Dri-1 based polymers | | | | | | | | |
| 24 | − | − | − | = | = | + | = | + |
| 25 | − | = | − | = | = | = | + | = |
| 26 | − | = | = | = | = | = | + | = |

[a]Unless otherwise mentioned, all polymers were neutralized to 90% level using AMP.
[b]100% neutralized.
[c]70% neutralized.
= not statistically different;
+ superior;
− inferior Based on the results shown in Table 3, all samples were considered to provide adequate subjective performance to warrant further testing of objective performance.

TABLE 10

Shampoo removability of representative starch polymers as compared to AMPHOMER ® polymer

| Sample | Stiffness after shampooing | Flake after shampooing | Dry feel after shampooing |
|---|---|---|---|
| Example 17 | + | + | + |
| Example 20 | + | = | = |

= not statistically different;
+ superior;
− inferior

Based on the subjective test results shown in Table 10, all samples were considered to provide overall statistically superior shampoo removability compared to AMPHOMER® polymer.

B. Determination of Spray Rate
Materials/Equipment:
Vented fume hood
Safety glasses
Top loading balance (0.01 gram accuracy)
Seconds' timer
PROCEDURE: Run In Duplicate
AEROSOL HAIR SPRAY
1 Weigh can of hair spray and record weight.
2 Place can in fume hood. Using constant pressure, depress actuator for ten seconds.
3 Re-weigh can and record weight.

Calculation: Initial Weight−Weight After Spraying=grams/second

Note: if duplicates do not agree to within 0.03 g/sec, repeat procedure
Non-Aerosol Hair Spray
1 Weigh pump bottle of hair spray and record weight.
2 Place bottle in fume hood. Consistently and completely, depress the actuator ten times ("bursts").
3 Re-weigh pump bottle and record weight.

Calculation: Initial Weight−Weight After Spraying=grams/"burst"

Note: if duplicates do not agree to within 0.03 g/"burst", repeat procedure

Valve Specification (procured from a company called Aptar)
Product VX-81
Body: VX Barbed 0.013 NOVT ARIAN
Stem: VX80 0.343 FC 1×0.013 ORIFICE
GASKET: VX 0.045 BUTYL CODE 501
SPRING: VS STAINLESS STEEL 0.018 OPEN C
CUP: HIPRO BNA PGFR GSK AL EP T/B D
TUBE: 0.122 ID
TUBE LENGTH: 09 00/16"
Actuator Specification (from Aptar)
REF NO: XL002838
PRODUCT: XL200 SHIP OUT
LABNUM: XL200 VX MISTY TAP 0.023 MISTY
BUTTON: VX XL 200 MISTY TAP WHITE
INSERT: 0.023 MISTY BLACK C. Procedure for Determining High Humidity Curl Retention (HHCR)

The following procedures were used to conduct the evaluations of the objective performance of the polyglucose polymers of the present invention as determined by high humidity curl retention. The high humidity curl retention properties of hair styling compositions including polyglucose polymers of the present invention were measured. The tests were each conducted at 72° F. (22° C.) and 90% Relative Humidity over a period of 24 hours. The tests were performed on 10" long×2-gram swatches of European virgin brown hair (9 replicate swatches per sample). Curl retention testing is run in a humidity chamber set at 70° F./90% Relative Humidity for a total of 24 hours. Readings for % Curl Retention are read and recorded at time intervals of 15, 30, 60, 90 min, 2, 3, 4, 5, and 24 hrs. The hair styling compositions were tested according to the following procedures:

1. Wet hair swatch, comb through to remove tangles and squeeze out excess water (run swatch between thumb and index finger).
2. Apply sample to swatch, gently "work into" swatch and comb through.
3. Roll swatch on ½" diameter Teflon mandrel. Carefully remove rolled swatch from mandrel and secure with two hair clips.
4. Place curls on tray and dry in oven overnight.
5. Remove dried curls from oven and let cool to room temperature.
6. Suspend curls, from bound end of swatch, on graduated clear, transparent curl retention boards.

7. Remove clips from curls and gently unwind with glass rod making sure to "break" the curl.
8. Take initial curl length readings before placing boards and curls into environmental chamber (70° F., 90% relative humidity).
9. Record curl lengths at the 15, 30, 60, 90, 2, 3, 4, 5, and hour time intervals.
10. At conclusion of test, remove boards and curls from chamber.
11. Clean used hair swatches.
12. Calculate % Curl Retention and comparison of samples.

The Samples were prepared as follows:

HHCR was run in a constant temperature and humidity chamber. Curls were rolled on a mandrel and allowed to dry overnight. The curls were then sprayed with the polymer solutions (3.5 wt % polymer using 80% VOC ethanol-water and 40% DME) and allowed to dry. Then the curls were hung on a board placed in the oven and the percent of curl loss was tracked over 24 hrs.

The high humidity curl retention properties of hair styling compositions including polyglucose polymers of the present invention according to the Examples as shown in the following Tables as indicated were measured and compared to the use of AMPHOMER® polymer in the same hair styling composition.

TABLE 4

HHCR results of Glucidex-1 based starch acetate succinate octenyl succinates of Examples 6-10 made using NaOAc as catalyst (using 3.5 wt % polymer) at 90% neutralization level compared to AMPHOMER ® polymer using 3.5% polymer using 80% VOC ethanol-water and 40% DME at 95% confidence level

| Example No. | 5 hrs | 24 hrs |
| --- | --- | --- |
| Example 6 | 82 (=) | 82 (=) |
| Example 7 | 82 (=) | 80 (=) |
| Example 8 | 83 (=) | 81 (=) |
| Example 9 | 81 (=) | 78 (=) |
| Example 10 | 73 (=) | 71 (=) |
| Amphomer | 76 | 74 |

= not statistically different;
+ superior;
− inferior

As shown in Table 4, all Examples provided statistically equal HHCR performance compared to AMPHOMER® polymer.

TABLE 5

HHCR results of Glucidex-1 based starch acetate succinate octenyl succinates of Examples 11-13 made using NaOH as catalyst (using 3.5 wt % polymer) at 90% neutralization level compared to AMPHOMER ® polymer using 3.5% polymer using 80% VOC ethanol-water and 40% DME at 95% confidence level

| Example No. | 5 hrs | 24 hrs |
| --- | --- | --- |
| Example 11 | 71 (=) | 67 (=) |
| Example 12 | 79 (=) | 72 (=) |
| Example 13 | 72 (=) | 70 (=) |
| Amphomer | 72 | 66 |

= not statistically different;
+ superior;
− inferior

As shown in Table 5, all Examples provided statistically equal HHCR performance compared to AMPHOMER® polymer.

TABLE 6

HHCR results of Glucidex-1 based starch acetate phthalate octenyl succinates of Examples 15 and 16 made using NaOAc as catalyst (using 4 wt % polymer) compared to AMPHOMER ® polymer using 4.0% polymer using 80% VOC ethanol-water and 40% DME at 95% confidence level

| Example No. | 5 hrs | 24 hrs |
| --- | --- | --- |
| 15[a] | 31 (−) | 22 (−) |
| 15[b] | 84 (=) | 83 (=) |
| 16[a] | 31 (−) | 25 (−) |
| 16[b] | 83 (=) | 81 (=) |
| Amphomer | 90 | 89 |

[a]Polymer was neutralized to 100% level using AMP;
[b]70% neutralized.
= not statistically different;
+ superior;
− inferior As shown in Table 6, the Examples having 70% neutralization provided statistically equal HHCR performance compared to AMPHOMER® polymer. On the other hand, the Examples having 100% neutralization had poor HHCR performance.

TABLE 7

HHCR results of Glucidex-2 based starch acetate succinate octenyl succinates of Examples 20 and 21 (using 3.5 wt % polymer) at 90% neutralization level at 90% neutralization level compared to AMPHOMER ® using 3.5% polymer using 80% VOC ethanol-water and 40% DME at 95% confidence level

| Example No. | 5 hrs | 24 hrs |
| --- | --- | --- |
| Example 20 | 30 (−) | 19 (−) |
| Example 21 | 64 (=) | 56 (−) |
| Amphomer | 76 | 74 |

= not statistically different;
+ superior;
− inferior

As shown in Table 7, Example 20 had poor HHCR performance compared to AMPHOMER® polymer at 5 hrs, while Examples 20 and 21 each had poor HHCR performance compared to AMPHOMER® polymer at 24 hrs.

TABLE 8

HHCR results of Star Dri-1 based starch acetate succinate octenyl succinates of Examples 24-26 (using 3.5 wt % polymer) at 90% neutralization level compared to AMPHOMER ® polymer using 3.5% polymer using 80% VOC ethanol-water and 40% DME at 95% confidence level

| Example No. | 5 hrs | 24 hrs |
| --- | --- | --- |
| Example 24 | 52 (−) | 45 (−) |
| Example 25 | 52 (−) | 48 (−) |
| Example 26 | 66 (=) | 63 (=) |
| Amphomer | 71 | 69 |

As shown in Table 8, Examples 24 and 25 provided poor HHCR performance compared to AMPHOMER® polymer, while Example 26 provided performance statistically equal to AMPHOMER® polymer.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described herein, the invention is not intended to be limited to the details shown. Rather, various modifications may be made in the details within the range and scope of equivalents of the claims and without departing from the spirit and scope of the invention.

I claim:

1. A hair fixative composition comprising:
   (a) at least one carboxylated starch ester based polyglucose polymer having the following structure (I):

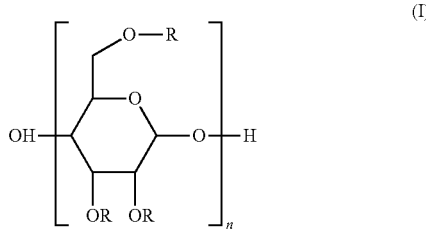

(I)

wherein R=H, $R_H$ or $R_A$ or combinations thereof, wherein at least one R is $R_A$ and wherein $R_H$ is —CO—$R^1$, wherein $R^1$ is a $C_1$-$C_3$ alkyl group; and $R_A$ is (a) —CO—$CH_2$—CH($R^2$)—COOH, wherein $R^2$=H or a $C_6$-$C_{18}$ alkenyl group, or b) —CO—CH=CH—COOH, or c) —CO—CH—C(=$CH_2$)—COOH, or d) —CO—$C_6H_4$—COOH, or e) —CO—$C_6H_8$—COOH; and wherein n=10-150;
   said at least one carboxylated starch ester based polyglucose polymer being obtained by reacting:
   (a)(i) at least one starch selected from the group consisting of maltodextrins;
   (a)(ii) at least one acyclic anhydride; and
   (a)(iii) at least two cyclic anhydrides;
   (b) an alcohol based solvent system, wherein the alcohol based solvent system comprises at least one $C_1$-$C_6$ straight or branched chain alcohol or mixtures thereof; and
   (c) at least one cosmetically acceptable additive;
   wherein the at least one carboxylated starch ester based polyglucose polymer (a) is from about 1 to about 10 wt % soluble in the alcohol based solvent system (b).

2. The hair fixative composition of claim 1, wherein the maltodextrin has a dextrose equivalent from 1 to 25.

3. The hair fixative composition of claim 1, wherein the at least one acyclic anhydride is selected from the group consisting of acetic anhydride, propionic anhydride, butyric anhydride, and mixtures thereof.

4. The hair fixative composition of claim 1, wherein the starch is a potato or corn maltodextrin having a dextrose equivalent of about 5 or more, wherein the at least one acyclic anhydride is selected from the group consisting of acetic anhydride, propionic anhydride, butyric anhydride, and mixtures thereof, and wherein the at least two cyclic anhydrides are selected from the group consisting of succinic anhydride, alkenyl succinic anhydrides, maleic anhydride, itaconic anhydride, phthalic anhydride, and tetrahydrophthalic anhydride.

5. The hair fixative composition of claim 1, wherein said solvent system (b) comprises at least of 80% alcohol.

6. The hair fixative composition of claim 1, wherein the alcohol based solvent system of (b) further comprises water, one or more propellants, or one or more non-alcohol, non-aqueous solvents, or mixtures thereof.

7. The hair fixative composition according to claim 1, wherein the alcohol based solvent system comprises ethanol and water.

8. The hair fixative composition according to claim 7, which further comprises dimethyl ether.

9. The hair fixative composition of claim 1, wherein the at least one carboxylated starch ester based polyglucose polymer is present in the hair fixative composition in an amount from 1 weight percent to 10 weight percent, based on the weight of the hair fixative composition.

10. The hair fixative composition of claim 1, wherein the at least one carboxylated starch ester based polyglucose polymer is at least 50% neutralized.

11. The hair fixative composition of claim 1, wherein the at least one cosmetically acceptable additive of (c) is selected from the group consisting of one or more hair fixative polymers, plasticizers, UV absorbers, dyes, perfumes, preservatives, viscosity modifiers, vitamins, sunscreen actives, moisturizers, anti-itch or anti-dandruff ingredients, and mixtures thereof.

12. The hair fixative composition of claim 1, wherein the hair fixative composition is an aerosol hairspray or a non-aerosol hairspray.

13. A method of preparing a hair fixative composition of claim 1, said method comprising:
   (a) reacting the at least one starch with the at least one acyclic anhydride to form at least one starch ester;
   (b) reacting the at least one starch ester with the at least two cyclic anhydrides to form the at least one carboxylated starch ester based polyglucose polymer;
   (c) dissolving or suspending the resulting at least one carboxylated starch ester based polyglucose polymer in the alcohol based solvent system;
   (d) optionally neutralizing the at least one carboxylated starch ester polyglucose polymer; and
   (e) adding at least one cosmetically acceptable additive.

* * * * *